United States Patent [19]

Debarre et al.

[11] 4,419,356

[45] Dec. 6, 1983

[54] 2,3,6,7-TETRAHYDROTHIAZOLO[3,2-A]PYRIMIDINE DERIVATIVES HAVING ANTI-RHEUMATIC PROPERTIES AND PHARMACEUTICAL COMPOSITIONS CONTAINING THEM

[75] Inventors: Francois Debarre, Antony; Jean-Louis Fabre, Paris; Daniel Farge, Thiais; Claude James, Paris, all of France

[73] Assignee: Rhone-Poulenc Industries, Paris, France

[21] Appl. No.: 285,845

[22] Filed: Jul. 22, 1981

[30] Foreign Application Priority Data

Jul. 24, 1980 [FR] France ............................... 80 16319
May 15, 1981 [FR] France ............................... 81 09724

[51] Int. Cl.³ .......................................... A61K 31/505
[52] U.S. Cl. ................................. 424/251; 544/278; 544/231
[58] Field of Search ................. 544/278, 231; 424/251

[56] References Cited

U.S. PATENT DOCUMENTS 3,888,983 6/1975 Baetz .................................. 544/278
4,219,649 8/1980 Knoll et al. ........................ 424/251

FOREIGN PATENT DOCUMENTS 778911 2/1972 Belgium ............................. 544/278
2140601 2/1972 Fed. Rep. of Germany ...... 544/278

OTHER PUBLICATIONS

Gabriel, S., Chem. Ber., 22, 1141, (1889).
Gabriel, S., Chem. Ber., 50, 804, (1917).
Gemmell et al., Agents et Actions, 9, 107, (1979).
Dieppe et al., Agents et Actions, 6, 618, (1976).

Primary Examiner—Donald G. Daus
Assistant Examiner—S. A. Gibson
Attorney, Agent, or Firm—Stevens, Davis, Miller & Mosher

[57] ABSTRACT

Thiazolo[3,2-a]pyrimidine derivative of the formula:

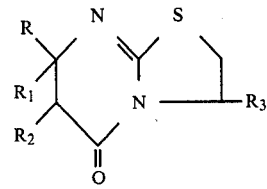

wherein R represents phenyl, alkyl of 1 through 4 carbon atoms, alkyl of 1 through 4 carbon atoms substituted by 1 through 3 halogen atom, alkenyl of 2 through 4 carbon atoms, or cycloalkyl of 3 through 6 carbon atoms and $R_1$ represents hydrogen, or R and $R_1$ each represent phenyl or unsubstituted alkyl of 1 through 4 carbon atoms, or R and $R_1$ together represent an alkylene radical of 4 or 5 carbon atoms, and $R_2$ and $R_3$ each represent hydrogen or unsubstituted alkyl of 1 through 4 carbon atoms, or R and $R_1$ each represent hydrogen, and one of $R_2$ and $R_3$ represents hydrogen and the other represents unsubstituted alkyl of 1 through 4 carbon atoms, or $R_2$ and $R_3$ both represent unsubstituted alkyl of 1 through 4 carbon atoms, are new compounds possessing pharmacological properties. They are especially useful in the treatment of rheumatic disease or allergic states, or as analgesics. Processes for the preparation of the compounds are described.

11 Claims, No Drawings

2,3,6,7-TETRAHYDROTHIAZOLO[3,2-A]PYRIMIDINE DERIVATIVES HAVING ANTI-RHEUMATIC PROPERTIES AND PHARMACEUTICAL COMPOSITIONS CONTAINING THEM

DESCRIPTION

This invention relates to new therapeutically useful 2,3,6,7-tetrahydrothiazolo[3,2-a]pyrimidine derivatives, to processes for their preparation and to pharmaceutical compositions containing them.

The 2,3,6,7-tetrahydrothiazolo[3,2-a]pyrimidine derivatives of the present invention are those compounds of the general formula:

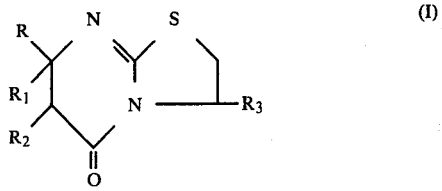

wherein either R represents a phenyl radical, an alkyl radical containing 1 to 4 carbon atoms optionally substituted by 1 to 3 halogen (preferably fluorine) atoms, an alkenyl radical containing 2 to 4 carbon atoms or a cycloalkyl radical containing 3 to 6 carbon atoms and $R_1$ represents a hydrogen atom, or R and $R_1$, which have the same or different significances, each represent a phenyl radical or an unsubstituted alkyl radical containing 1 to 4 carbon atoms, or R and $R_1$ together represent an alkylene radical containing 4 or 5 carbon atoms, and $R_2$ and $R_3$, which have the same or different significances, each represent a hydrogen atom or an unsubstituted alkyl radical containing 1 to 4 carbon atoms, or R and $R_1$ each represent a hydrogen atom, and one of $R_2$ and $R_3$ represents a hydrogen atom and the other represents an unsubstituted alkyl radical containing 1 to 4 carbon atoms, or $R_2$ and $R_3$ both represent an unsubstituted alkyl radical containing 1 to 4 carbon atoms.

It is understood that the alkyl radicals mentioned above or hereafter have straight- or branched-chains.

According to a feature of the present invention, compounds of the general formula (I) are prepared by reacting a halide of the general formula:

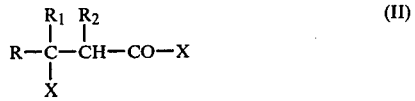

with a 2-amino-2-thiazoline (in equilibrium with its imine form) of the general formula:

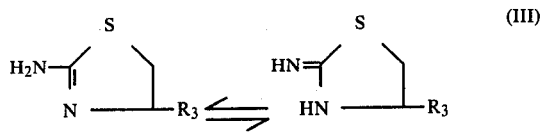

in which formulae R, $R_1$, $R_2$ and $R_3$ are as hereinbefore defined and X represents a halogen atom such as chlorine or bromine.

The reaction is generally carried out in an aromatic organic solvent (e.g. benzene, toluene or a xylene), a chlorinated solvent (e.g. chloroform, carbon tetrachloride or 1,2-dichloroethane), an ether (e.g. dioxan or tetrahydrofuran) or dimethylformamide, at a temperature between about 20° C. and the reflux temperature of the reaction mixture, in the presence of an acid-binding agent such as an inorganic base (e.g. an alkali metal bicarbonate) or an organic base (e.g. triethylamine).

The halides of the general formula (II) can be prepared, for example, by reacting a halogenating agent such as thionyl chloride with the corresponding β-hydroxyacid.

The 2-amino-2-thiazolines of general formula (III) can be prepared in accordance with the method described by S. Gabriel, Ber. 22, 1141 (1889), or the method described by S. Gabriel and H. Ohle, Ber. 50, 804 (1917).

According to another feature of the present invention, the compounds of general formula (I), with the exception of those wherein R and $R_1$ together form an alkylene radical, are prepared in accordance with one of the following processes:

(A) By reacting an acid halide of the general formula:

with a 2-amino-2-thiazoline of general formula (III), in which formulae R, $R_1$, $R_2$ and $R_3$ have the corresponding definitions and X represents a halogen atom such as chlorine or bromine.

The reaction is generally carried out in an aromatic organic solvent (e.g. benzene, toluene or a xylene), a chlorinated solvent (e.g. chloroform, carbon tetrachloride or 1,2-dichloroethane), an ether (e.g. dioxan or tetrahydrofuran) or dimethylformamide, at a temperature between about 20° C. and the reflux temperature of the reaction mixture, in the presence of an acid-binding agent such as an inorganic base (e.g. an alkali metal bicarbonate) or an organic base (e.g. triethylamine).

The halides of general formula (IV) can be prepared from the corresponding acids by any method which is in itself known and which does not affect the rest of the molecule.

(B) By reacting an ester of the general formula:

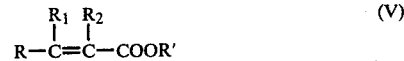

with a 2-amino-2-thiazoline of general formula (III), in which formulae R, $R_1$, $R_2$ and $R_3$ have the corresponding definitions and R' represents an alkyl radical containing 1 to 4 carbon atoms.

The reaction is generally carried out without a solvent or alternatively in an aromatic organic solvent, such as benzene, toluene or a xylene, at a temperature between about 50° C. and the reflux temperature of the reaction mixture, in the presence of an antioxidant such as hydroquinone.

The esters of the general formula (V) can be obtained from the corresponding acids by any method which is in itself known for obtaining an acrylic acid ester.

According to a still further feature of the present invention, the compounds of general formula (I) wherein $R_3$ represents a hydrogen atom are prepared by reacting 1,2-dibromoethane with a 4,5-dihydro-2-thiouracil of the general formula:

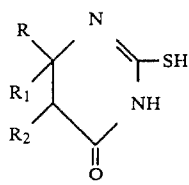

(VI)

(wherein R, R$_1$ and R$_2$ are as hereinbefore defined), preferably in an anhydrous organic solvent, such as dimethylformamide, at a temperature between about −10° and a maximum of 25° C. in the presence of an alkali metal hydride such as sodium hydride.

The 4,5-dihydro-2-thiouracils of general formula (VI) can be prepared in accordance with the method described by L. S. Sandakhcheiev and V. P. Mamaev, Izvest. Sibir. Otdel. Akad. Nauk. S.S.S.R. (1961), No. 7, pages 72–76; Chem. Abstracts 56, 24482.

The new products of general formula (I) so obtained by the aforedescribed processes can be purified by usual methods such as crystallisation and chromatography.

2,3-Dihydrothiazolo[3,2-a]pyrimidin-5-ones are known from Belgian Patent 778911; the products disclosed therein are described as having an analgesic activity.

The new compounds of general formula (I) possess valuable pharmacological properties which make them useful for the basic treatment of rheumatic disease, as anti-allergic agents and as analgesics.

In particular, they are active in rats at doses of between 10 and 100 mg/kg animal body weight, administered orally, against oedema of the paw caused by a reverse ARTHUS reaction [oedema caused by the subplantar injection of 50 μg of antiovalbumin rabbit serum, immediately followed by the intravenous injection of ovalbumin, in accordance with the technique of D. K. Gemmell et al., Agents et Actions, 9, 107 (1979)].

They are also active in rats at daily doses which are generally between 5 and 100 mg/kg animal body weight, administered orally for 7 days, against oedema of the paw caused by the subplantar injection of *Bordetella pertussis* (*Hemophilus pertussis*) into rats sensitised to this antigen, in accordance with the technique of P. A. Dieppe et al., Agents et Actions, 6, 618 (1976).

Some of them have been shown to be active at daily doses of between 20 and 80 mg/kg animal body weight, administered orally for 18 days, using the technique of experimental polyarthritis in rats, caused by the subplantar injection, into a back paw, of FREUND's complete adjuvant, according to F. Delbarre et al., C.R. Soc. Biol. 162, 58 (1968).

Their analgesic activity has been shown in mice at doses between 1 and 100 mg/kg animal body weight administered orally, in accordance with the technique of E. Siegmund et al, Proc. Soc. Exp. Biol. Med. 95, 729 (1957).

Furthermore, the compounds according to the invention exhibit a low toxicity. In mice, the acute toxicity (expressed by its LD$_{50}$) is generally between 300 and 900 mg/kg or above 900 mg/kg animal body weight, administered orally.

Of particular importance are the compounds of general formula (I) wherein R represents an unsubstituted alkyl radical containing 1 to 4 carbon atoms, a phenyl radical or a cycloalkyl radical containing 3 to 6 carbon atoms, and R$_1$ represents a hydrogen atom, or alternatively R and R$_1$ together form an alkylene radical containing 4 or 5 carbon atoms, and R$_2$ and R$_3$, which have the same or different significances, each represent a hydrogen atom or a methyl radical.

Of more particular importance are the compounds of general formula (I) wherein R represents a methyl, ethyl, phenyl or cyclohexyl radical and R$_1$ represents a hydrogen atom, or alternatively R and R$_1$ together represent the pentamethylene radical, R$_2$ represents a hydrogen atom, and R$_3$ represents a hydrogen atom or the methyl radical.

The following compounds are of outstanding importance: 7-methyl-5-oxo-2,3,6,7-tetrahydro-5H-thiazolo[3,2-a]pyrimidine, 7-ethyl-5-oxo-2,3,6,7-tetrahydro-5H-thiazolo[3,2-a]pyrimidine, 7-cyclohexyl-5-oxo-2,3,6,7-tetrahydro-5H-thiazolo[3,2-a]pyrimidine, 5-oxo-2,3,6,7-tetrahydro-spiro{5H-thiazolo[3,2-a]pyrimidine-7,1'-cyclohexane}, 3,7-dimethyl-5-oxo-2,3,6,7-tetrahydro-5H-thiazolo[3,2-a]pyrimidine and 5-oxo-7-phenyl-2,3,6,7-tetrahydro-5H-thiazolo[3,2,-a]pyrimidine.

The following Examples illustrate the preparation of thiazolo[3,2-a]pyrimidine derivatives of the present invention.

EXAMPLE 1

A solution of cinnamoyl chloride (3.33 g) in chloroform (1.7 cc) is added dropwise, in the course of 3 minutes, at a temperature of about 20° C. to a solution of 2-amino-2-thiazoline (2.04 g) and triethylamine (2.8 cc) in chloroform (7.2 cc). The reaction mixture, the temperature of which is then 30° C., is subsequently heated under reflux for 1 hour 40 minutes and then cooled to 4° C. with the aid of an ice bath. The resulting crystals are filtered off, washed twice with chloroform (5 cc in total) and discarded. The organic filtrates are combined and washed twice with distilled water (5 cc in total), dried over anhydrous sodium sulphate, treated with decolorising charcoal (0.2 g) and filtered, and the filtrate is concentrated to a volume of 9 cc. The concentrate is chromatographed on a column of diameter 1.5 cm containing neutral alumina (0.12–0.15 mm; 28 g). Elution is carried out with a chloroform/cyclohexane mixture (40/60 by volume), 50 cc fractions being collected. The first 4 fractions are combined and concentrated to dryness under reduced pressure (20 mm Hg; 2.7 kPa) at 40° C. This yields a crude product (1.1 g) which is dissolved in boiling ethanol (1.35 cc). After cooling at 4° C. for 1 hour, the resulting crystals are filtered off, washed twice with ethanol cooled to about 5° C. (0.4 cc in total) and dried under reduced pressure (20 mm Hg; 2.7 kPa) at a temperature of about 20° C. in the presence of potassium hydroxide pellets. This yields 5-oxo-7-phenyl-2,3,6,7-tetrahydro-5H-thiazolo[3,2-a]pyrimidine (0.6 g) in the form of a white solid melting at 115° C.

EXAMPLE 2

A mixture of ethyl cinnamate (299.5 g), 2-amino-2-thiazoline (173.4 g) and hydroquinone (2 g) is heated at 110° C. for 24 hours. After cooling to a temperature of about 20° C., methylene chloride (800 cc) is added and the mixture is extracted 5 times with a 2 N aqueous solution of hydrogen chloride (2500 cc in total). The combined aqueous solutions are brought to pH 8 by adding a 10 N aqueous solution of sodium hydroxide and are then extracted 4 times with methylene chloride (2000 cc in total). The organic extracts are combined and dried over anhydrous sodium sulphate and filtered, and the filtrate is concentrated to dryness under reduced pressure (20 mm Hg; 2.7 kPa) at 40° C. The resulting residue (113 g) is chromatographed on a column of diameter 7.5 cm containing silica (0.06-0.2 mm; 1100 g). Elution is carried out with methylene chloride, 1000 cc fractions being collected. The first 2 fractions are discarded and the following 14 fractions are combined and concentrated to dryness under reduced pressure (20 mm Hg; 2.7 kPa) at 40° C. This yields a crude product (26 g) which is dissolved in boiling ethanol (75 cc) to which decolorising charcoal (1 g) has been added. After hot filtration, the filtrate is cooled at 4° C. for 12 hours. The resulting crystals are filtered off, washed twice with ethanol cooled to about 5° C. (20 cc in total) and dried under reduced pressure (20 mm Hg; 2.7 kPa) at a temperature of about 20° C., in the presence of potassium hydroxide pellets. This yields 5-oxo-7-phenyl-2,3,6,7-tetrahydro-5H-thiazolo[3,2-a]pyrimidine (21.6 g) in the form of white crystals melting at 113° C.

EXAMPLE 3

A 54.5% dispersion of sodium hydride (51.7 g) in oil is added, in the course of 25 minutes, to a solution cooled to 8° C. of 4-phenyl-4,5-dihydro-2-thiouracil (110 g) in anhydrous dimethylformamide (1200 cc), care being taken that the temperature of the reaction mixture remains below 15° C. Twenty five minutes after the addition has ended, 1,2-dibromoethane (91.7 cc) is run dropwise into the reaction mixture in the course of 30 minutes, the temperature always being kept below 15° C. Stirring is continued for a further 2 hours and the temperature of the mixture is left to return to about 20° C. The reaction mixture is then brought to pH 5 by adding a 1 N aqueous solution of hydrogen chloride and is then concentrated to dryness under reduced pressure (1 mm Hg; 0.13 kPa) at a temperature below 50° C. The residue is taken up in distilled water (500 cc) and the solution is brought to pH 9 with the aid of a 10 N aqueous solution of sodium hydroxide and extracted 3 times with methylene chloride (1400 cc in total). The organic phase thus obtained is washed with distilled water (300 cc), dried over anhydrous sodium sulphate and filtered and the filtrate is concentrated to dryness under reduced pressure (20 mm Hg; 2.7 kPa) at 40° C. The resulting residue (111 g) is dissolved in methylene chloride (1100 cc) and chromatographed on a column of diameter 6.8 cm containing basic alumina (0.05–0.16 mm; 1100 g). Elution is carried out with methylene chloride, 250 cc fractions being collected. The first 3 fractions are discarded; the following 3 fractions are combined and concentrated to dryness under reduced pressure (20 mm Hg; 2.7 kPa) at 40° C. The residue obtained (32.5 g) is dissolved in a boiling mixture of ethanol (70 cc) and diisopropyl ether (70 cc). After cooling, the resulting crystals are filtered off and dried under reduced pressure (20 mm Hg; 2.7 kPa) at a temperature of about 20° C. This yields a crude product (13.6 g) melting at 110° C., which is combined with a product (1.4 g) prepared in the same manner in another operation, and the combined product is dissolved in boiling ethanol (60 cc). The solution is filtered hot and the filtrate is then cooled at 4° C. for 1 hour. The resulting crystals are filtered off, washed with ethanol (5 cc) and then with diisopropyl ether (5 cc) and dried under reduced pressure (20 mm Hg; 2.7 kPa) at a temperature of about 20° C. in the presence of potassium hydroxide pellets. This yields 5-oxo-7-phenyl-2,3,6,7-tetrahydro-5H-thiazolo[3,2-a]pyrimidine (13 g) in the form of white crystals melting at 112° C.

EXAMPLE 4

A solution of crotonoyl chloride (440 g) in chloroform (1200 cc) is added dropwise, in the course of 47 minutes, to a solution of 2-amino-2-thiazoline (504 g) and triethylamine (590 cc) and triethylamine (590 cc) in chloroform (1200 cc). The reaction mixture, the temperature of which is then 63° C., is subsequently heated under reflux for 16 hours. After cooling to about 20° C., the resulting crystals are filtered off, washed twice with chloroform (100 cc in total) and discarded. The organic filtrates are combined and concentrated to dryness under reduced pressure (20 mm Hg; 2.7 kPa) at 40° C. and the residue is taken up in ethyl acetate (700 cc). The resulting crystals are filtered off, washed with a mixture of ethyl acetate and methanol (90/10 by volume; 200 cc) and discarded. The organic filtrates are combined and chromatographed on a column of diameter 9 cm containing silica (0.06–0.2 mm) (3.5 kg), elution being carried out with ethyl acetate and 1000 cc fractions being collected. The first 5 fractions are discarded; the following 6 fractions are combined and concentrated to dryness under reduced pressure (20 mm Hg; 2.7 kPa) at 40° C. This yields a crude product (124 g) melting at 91° C., which is divided into 3 equal batches to be chromatographed separately, in each case on a column of diameter 6 cm containing silica (0.040–0.063 mm; 480 g). Elution is carried out with ethyl acetate under a pressure of 0.5 bar (51 kPa), 200 cc fractions being collected. The first 8 fractions are discarded; the following 10 fractions are combined and concentrated to dryness under reduced pressure (20 mm Hg; 2.7 kPa) at 40° C. This yields a product (109 g) in the form of white crystals melting at 93° C., which is dissolved in boiling ethyl acetate (160 cc) to which decolorising charcoal (1 g) has been added. After hot filtration, the filtrate is cooled at 4° C. for 2 hours; the resulting crystals are filtered off, washed 3 times with diisopropyl ether cooled to about 5° C. (100 cc in total) and dried under reduced pressure (20 mm Hg; 2.7 kPa) at a temperature of about 20° C. in the presence of potassium hydroxide pellets. This yields 7-methyl-5-oxo-2,3,6,7-tetrahydro-5H-thiazolo[3,2-a]pyrimidine (96.8 g) in the form of white crystals melting at 96° C.

EXAMPLE 5

A solution of pent-2-enoyl chloride (50 g) in chloroform (300 cc) is added dropwise, in the course of 30 minutes, to a solution of 2-amino-2-thiazoline (50.6 g) and triethylamine (59 cc) in chloroform (350 cc). The reaction mixture, the temperature of which is then 49° C., is subsequently heated under reflux for 16 hours. After cooling to about 20° C., the resulting crystals are filtered off and discarded. The organic filtrate is concentrated to dryness under reduced pressure (20 mm Hg; 2.7 kPa) at 40° C. and the residue is then taken up in acetone (250 cc). The resulting crystals are filtered off, washed twice with acetone (60 cc in total) and discarded. The organic filtrates are concentrated to dryness under reduced pressure (20 mm Hg; 2.7 kPa) at 40° C., and the residue is chromatographed on a column of diameter 7 cm containing silica (0.06–0.2 mm; 820 g), elution being carried out with ethyl acetate and 1000 cc fractions being collected. The first fraction is discarded; the following 4 fractions are combined and concentrated to dryness under reduced pressure (20 mm Hg;

2.7 kPa) at 40° C. This yields a crude product (31 g) in the form of an oil. which is added to a product (6 g) prepared in the same manner in another operation, and the combined product is chromatographed on a column of diameter 6 cm containing silica (0.040–0.063 mm; 480 g). Elution is carried out with an ethyl acetate/cyclohexane mixture (70/30 by volume) under a pressure of 0.5 bar (51 kPa), 200 cc fractions being collected. The first 6 fractions are discarded; the following 6 fractions are combined and concentrated to dryness under reduced pressure (20 mm Hg; 2.7 kPa) at 40° C. This yields a product (21.7 g) which is dissolved in boiling diisopropyl ether (50 cc) to which decolorising charcoal (0.2 g) has been added. After hot filtration, the filtrate is cooled at 4° C. for 1 and a half hours; the resulting crystals are filtered off, washed twice with diisopropyl ether cooled to about 5° C. (20 cc in total) and dried under reduced pressure (20 mm Hg; 2.7 kPa) at a temperature of about 20° C. in the presence of potassium hydroxide pellets. This yields 7-ethyl-5-oxo-2,3,6,7-tetrahydro-5H-thiazolo[3,2-a]-pyrimidine (18.6 g) in the form of white crystals melting at 60° C.

EXAMPLE 6

A solution of 4-methylpent-2-enoyl chloride (35.5 g) in chloroform (200 cc) is added dropwise, in the course of 20 minutes, to a solution of 2-amino-2-thiazoline (32.2 g) and triethylamine (37.7 cc) in chloroform (200 cc). The reaction mixture, the temperature of which is then 53° C., is subsequently heated under reflux for 16 hours. After cooling to about 20° C., the resulting crystals are filtered off and discarded. The organic filtrate is concentrated to dryness under reduced pressure (20 mm Hg; 2.7 kPa) at 40° C. and the residue is taken up in acetone (200 cc). The resulting crystals are filtered off, washed twice with acetone (60 cc in total) and discarded. The organic filtrates are concentrated to dryness under reduced pressure (20 mm Hg; 2.7 kPa) at 40° C. and the residue is chromatographed on a column of diameter 4 cm containing neutral alumina (0.12–0.15 mm; 550 g). Elution is carried out with ethyl acetate, 500 cc fractions being collected. The first fraction is discarded; the following 2 fractions are combined and concentrated to dryness under reduced pressure (20 mm Hg; 2.7 kPa) at 40° C. This yields a crude product (25 g) in the form of an oil, which is chromatographed again on a column of diameter 6 cm containing silica (0.040–0.063 mm; 480 g). Elution is carried out with an ethyl acetate/cyclohexane mixture (60/40 by volume) under a pressure of 0.5 bar (51 kPa), 250 cc fractions being collected. The first 7 fractions are discarded; the following 9 fractions are combined and concentrated to dryness under reduced pressure (20 mm Hg; 2.7 kPa) at 40° C. This yields a product (15 g) which is dissolved in boiling diisopropyl ether (50 cc) to which decolorising charcoal (0.2 g) has been added. After hot filtration, the filtrate is cooled at 4° C. for 1 hour; the resulting crystals are filtered off, washed twice with diisopropyl ether cooled to about 5° C. (20 cc in total) and dried under reduced pressure (20 mm Hg; 2.7 kPa) at a temperature of about 20° C. in the presence of potassium hydroxide pellets. This yields 7-isopropyl-5-oxo-2,3,6,7-tetrahydro-5H-thiazolo[3,2-a]pyrimidine (11.8 g) in the form of white crystals melting at 50.6° C.

EXAMPLE 7

A solution of hex-2-enoyl chloride (79.5 g) in chloroform (750 cc) is added dropwise, in the course of 75 minutes, to a solution of 2-amino-2-thiazoline (61.2 g) and triethylamine (84.2 cc) in chloroform (600 cc). The reaction mixture, the temperature of which is then 40° C., is subsequently heated under reflux for 45 minutes and, after cooling to about 20° C., washed 4 times with distilled water (1200 cc in total). The organic phase is dried over anhydrous magnesium sulphate, treated with decolorising charcoal (10 g) and filtered, and the filtrate is concentrated to dryness under reduced pressure (20 mm Hg; 2.7 kPa) at 40° C. This yields an oily residue (110 g) which is chromatographed on a column of diameter 5.1 cm containing alumina (0.12–0.15 mm; 1.1 kg). Elution is carried out with methylene chloride, 1000 cc of eluate being collected. The eluate is concentrated to dryness under reduced pressure (20 mm Hg; 2.7 kPa) at 40° C. This yields a product (25 g) which is chromatographed again on a column of diameter 3.2 cm containing alumina (0.12–0.15 mm; 250 g) in the presence of cyclohexane. Elution is carried out with chloroform/cyclohexane mixtures, 200 cc fractions being collected. The first 3 fractions (elution solvent:chloroform/cyclohexane, 20/80 by volume) are discarded; the following 4 fractions (elution solvent:chloroform/cyclohexane, 30/70 by volume) and the last 3 fractions (elution solvent:chloroform/cyclohexane, 40/60 by volume) are combined and concentrated to dryness under reduced pressure (20 mm Hg; 2.7 kPa) at 40° C. This yields a residue (14.7 g) which is taken up in diethyl ether (50 cc) and the solution is filtered. After filtration, the filtrate is concentrated to dryness under reduced pressure (20 mm Hg; 2.7 kPa) at 40° C. and the residue is chromatographed on a column of diameter 2.4 cm containing alumina (0.12–0.15 mm; 100 g). 100 cc fractions are eluted under the following conditions:

Fraction 1: (pure cyclohexane)
Fraction 2: (pure cyclohexane)
Fractions 3 and 4: (cyclohexane/chloroform: 90/10 by volume)
Fractions 5 and 6: (cyclohexane/chloroform: 80/20 by volume)
Fractions 7 and 8: (cyclohexane/chloroform: 70/30 by volume)

Fraction 1 is discarded; fractions 2 to 8 are combined and concentrated to dryness under reduced pressure (20 mm Hg; 2.7 kPa) at 40° C. This yields a product (4.3 g) which is dissolved in boiling petroleum ether (b.p. 40°–65° C.; 20 cc). After cooling at 4° C. for 16 hours, the resulting crystals are filtered off, washed with petroleum ether (b.p. 40°–65° C.) cooled to about 5° C. (5 cc), and dried under reduced pressure (20 mm Hg; 2.7 kPa) at a temperature of about 20° C. in the presence of potassium hydroxide pellets. This yields 5-oxo-7-propyl-2,3,6,7-tetrahydro-5H-thiazolo[3,2-a]pyrimidine (2.5 g) in the form of white crystals melting at 47° C.

EXAMPLE 8

A solution of 3-t-butylacryloyl chloride (13.1 g) in chloroform (60 cc) is added dropwise, in the course of 25 minutes, to a solution of 2-amino-2-thiazoline (10.25 g) and triethylamine (12.6 cc) in chloroform (60 cc). The reaction mixture, the temperature of which is then 51° C., is subsequently heated under reflux for 16 hours. After cooling to about 20° C., the resulting crystals are filtered off and discarded. The organic filtrate is concentrated to dryness under reduced pressure (20 mm Hg; 2.7 kPa) at 35° C. and the residue is then taken up in acetone (110 cc). The resulting crystals are filtered off, washed twice with acetone (50 cc in total) and discarded. The organic filtrates are combined and concentrated to dryness under reduced pressure (20 mm Hg; 2.7 kPa) at 30° C. The residue is chromatographed on a column of diameter 3.5 cm containing silica (0.063–0.2 mm; 200 g), elution being carried out with a mixture of ethyl acetate and cyclohexane (50/50 by volume) and 50 cc fractions being collected. The first 3 fractions are discarded and the following 6 fractions are combined and concentrated to dryness under reduced pressure (20 mm Hg; 2.7 kPa) at 30° C. This yields a crude product (4 g) which is added to a product (2 g) prepared in the same manner in another operation, and the combined product is dissolved in boiling diisopropyl ether (24 cc) to which decolorising charcoal (0.1 g) has been added. After hot filtration, the filtrate is cooled at 4° C. for 2 hours; the resulting crystals are filtered off, washed twice with diisopropyl ether cooled to about 5° C. (10 cc in total) and dried under reduced pressure (20 mm Hg; 2.7 kPa) at a temperature of about 20° C. in the presence of potassium hydroxide pellets. This yields 7-t-butyl-5-oxo-2,3,6,7-tetrahydro-5H-thiazolo-[3,2-a]pyrimidine (4.3 g) in the form of white crystals melting at 112° C.

EXAMPLE 9

A solution of 5-methylhex-2-enoyl chloride (142.5 g) in chloroform (600 cc) is added dropwise, in the course of 35 minutes, to a solution of 2-amino-2-thiazoline (106 g) and triethylamine (124 cc) in chloroform (700 cc). The reaction mixture, the temperature of which is then 63° C., is subsequently heated under reflux for 16 hours. After cooling to about 20° C., the resulting crystals are filtered off and discarded. The organic filtrate is concentrated to dryness under reduced pressure (20 mm Hg; 2.7 kPa) at 45° C. and the residue is taken up in acetone (1000 cc). The resulting crystals are filtered off and discarded. The organic filtrate is concentrated to dryness under reduced pressure (20 mm Hg; 2.7 kPa) at 40° C. and the residue is chromatographed on a column of diameter 7 cm containing silica (0.06–0.2 mm; 1250 g), elution being carried out with ethyl acetate and 500 cc fractions being collected. The first 8 fractions are discarded; the following 9 fractions are combined and concentrated to dryness under reduced pressure (20 mm Hg; 2.7 kPa) at 40° C. This yields a crude product (107 g) which is distilled under reduced pressure (0.7 mm Hg; 0.09 kPa) at a temperature between 135° C. and 142° C. The product obtained (33 g) is chromatographed on a column of diameter 6 cm containing silica (0.040–0.063 mm; 480 g). Elution is carried out with an ethyl acetate/cyclohexane mixture (50/50 by volume) under a pressure of 0.5 bar (51 kPa), 250 cc fractions being collected. The first 7 fractions are discarded; the following 10 fractions are combined and concentrated to dryness under reduced pressure (1 mm Hg; 0.13 kPa) at a temperature of 60° C. This yields 7-isobutyl-5-oxo-2,3,6,7-tetrahydro-5H-thiazolo[3,2-a]pyrimidine (27.8 g) in the form of a pale yellow oil (refractive index: $n_D^{23} = 1.545$).

EXAMPLE 10

A solution of sorboyl chloride (342 g) in chloroform (1600 cc) is added dropwise, in the course of 75 minutes, to a solution of 2-amino-2-thiazoline (294 g) and triethylamine (368 cc) in chloroform (1600 cc). The reaction mixture, the temperature of which is then 52° C., is subsequently heated under reflux for 16 hours. After cooling to about 20° C., the resulting crystals are filtered off and discarded. The organic filtrate is concentrated to dryness under reduced pressure (20 mm Hg; 2.7 kPa) at 35° C. and the residue is then taken up in acetone (1200 cc). The resulting crystals are once again filtered off and discarded. The organic filtrate is concentrated to dryness under reduced pressure (20 mm Hg; 2.7 kPa) at 40° C. and the residue is chromatographed on a column of diameter 6.5 cm containing neutral alumina (0.12–0.15 mm; 1620 g), elution being carried out with methylene chloride and 300 cc fractions being collected. The first 2 fractions are discarded; the following 5 fractions are combined and concentrated to dryness under reduced pressure (20 mm Hg; 2.7 kPa) at 40° C. This yields a crude product (56 g) in the form of an oil, which is chromatographed on a column of diameter 5 cm containing silica (0.063–0.2 mm; 560 g), elution being carried out with ethyl acetate and 200 cc fractions being collected. The first 4 fractions are discarded; the following 8 fractions are combined and concentrated to dryness under reduced pressure (20 mm Hg; 2.7 kPa) at 40° C. This yields a product (33.7 g) which is added to a product (5.2 g) prepared in the same manner in another operation. By distillation under reduced pressure (0.8 mm Hg; 0.11 kPa), a product (14.8 g) boiling at 165° C. is obtained. After the addition of hydroquinone (5 mg), the product is redistilled under reduced pressure (3.5 mm Hg; 0.47 kPa) under a nitrogen atmosphere. This yields 5-oxo-7-(prop-1-enyl)-2,3,6,7-tetrahydro-5H-thiazolo[3,2-a]pyrimidine (9.5 g) in the form of a pale yellow oil boiling at 202° C. (refractive index: $n_D^{23} = 1.581$).

EXAMPLE 11

A solution of 3-cyclopropylacryloyl chloride (24 g) in chloroform (90 cc) is added dropwise, in the course of 15 minutes, to a solution of 2-amino-2-thiazoline (21 g) and triethylamine (25.9 cc) in chloroform (90 cc). The reaction mixture, the temperature of which is then 63° C., is subsequently heated under reflux for 18 hours. After cooling to about 20° C., the resulting crystals are filtered off and discarded. The organic filtrate is concentrated to dryness under reduced pressure (20 mm Hg; 2.7 kPa) at 40° C. and the residue is taken up in acetone (260 cc). The resulting crystals are once again filtered off, washed twice with acetone (100 cc in total) and discarded. The combined organic filtrates are concentrated to dryness under reduced pressure (20 mm Hg; 2.7 kPa) at 30° C. and the residue is chromatographed on a column of diameter 4.7 cm containing silica (0.063–0.2 mm; 400 g), elution being carried out with a mixture of ethyl acetate and cyclohexane (50/50 by volume) and 300 cc fractions being collected. The first 8 fractions are discarded and the following 5 fractions are combined and concentrated to dryness under reduced pressure (20 mm Hg; 2.7 kPa) at 40° C. This yields a crude product (6 g) which is distilled under reduced pressure (2.5 mm Hg; 0.34 kPa). This yields a product (4.4 g) boiling at 172° C. after the addition of diisopropyl ether (15 cc) and cooling to a temperature of about 5° C., the resulting crystals are filtered off, washed twice with diisopropyl ether cooled to about 5° C. (5 cc in total) and dried under reduced pressure (20 mm Hg; 2.7 kPa) at a temperature of about 20° C. in the presence of potassium hydroxide pellets. This yields 7-cyclopropyl-5-oxo-2,3,6,7-tetrahydro-5H-thiazolo[3,2-a]-pyrimidine (3.5 g) in the form of white crystals melting at 60° C.

EXAMPLE 12

A solution of 3-cyclohexylacryloyl chloride (83.4 g) in chloroform (340 cc) is added dropwise, in the course of 30 minutes, to a solution of 2-amino-2-thiazoline (55.4 g) and triethylamine (68 cc) in chloroform (340 cc). The reaction mixture, the temperature of which is then 51° C., is subsequently heated under reflux for 15 hours. After cooling to about 20° C., the resulting crystals are filtered off and discarded. The organic filtrate is concentrated to dryness under reduced pressure (20 mm Hg; 2.7 kPa) at 45° C. and the residue is taken up in acetone (700 cc). The resulting crystals are once filtered off and discarded. The organic filtrate is concentrated to dryness under reduced pressure (20 mm Hg; 2.7 kPa) at 40° C. and the residue is chromatographed on a column of diameter 6.4 cm containing silica (0.06–0.2 mm; 1 kg), elution being carried out with ethyl acetate and 1000 cc fractions being collected. The first fraction is discarded; the following 3 fractions are combined and concentrated to dryness under reduced pressure (20 mm Hg; 2.7 kPa) at 40° C. This yields a crude product (72 g) which is chromatographed on a column of diameter 4.2 cm containing neutral alumina (0.12–0.15 mm; 610 g). Elution is carried out with a chloroform/cyclohexane mixture (50/50 by volume), 250 cc fractions being collected. The first fraction is discarded; the following 9 fractions are combined and concentrated to dryness under reduced pressure (20 mm Hg; 2.7 kPa) at 40° C. This yields a product (50.7 g) which is dissolved in boiling diisopropyl ether (250 cc) to which decolorising charcoal (0.5 g) has been added. After hot filtration, the filtrate is cooled at 4° C. for 3 hours; the resulting crystals are filtered off, washed twice with diisopropyl ether cooled to about 5° C. (30 cc in total) and dried under reduced pressure (20 mm Hg; 2.7 kPa) at a temperature of about 20° C. in the presence of potassium hydroxide pellets. This yields 7-cyclohexyl-5-oxo-2,3,6,7-tetrahydro-5H-thiazolo[3,2-a]pyrimidine (40.7 g) in the form of white crystals melting at 90° C.

EXAMPLE 13

A solution of methacryloyl chloride (72.2 g) in chloroform (480 cc) is added dropwise, in the course of 50 minutes, to a solution of 2-amino-2-thiazoline (82.8 g) and triethylamine (97 cc) in chloroform (400 cc). The reaction mixture, the temperature of which is then 54° C., is subsequently heated under reflux for 1 hour. After cooling to about 20° C., the resulting crystals are filtered off and discarded. The organic filtrate is concentrated to dryness under reduced pressure (20 mm Hg; 2.7 kPa) at 45° C. and the residue is taken up in ethyl acetate (400 cc). The resulting crystals are once again filtered off, washed twice with ethyl acetate (100 cc in total) and discarded. The combined organic solutions are concentrated to dryness under reduced pressure (20 mm Hg; 2.7 kPa) at 40° C. and the residue is chromatographed on a column of diameter 6.2 cm containing silica (0.06–0.2 mm; 1 kg), elution being carried out with ethyl acetate/cyclohexane mixtures and 500 cc fractions being collected. The first 8 fractions, originating from elution with a 20/80 by volume mixture, and the following 7 fractions, originating from elution with a 25/75 by volume mixture, are discarded. The following 8 fractions, originating from elution with a 30/70 by volume mixture, are combined and concentrated to dryness under reduced pressure (20 mm Hg; 2.7 kPa) at 40° C. This yields a product (27.9 g) which is divided into 2 equal batches to be chromatographed separately, in each case on a column of diameter 5 cm containing silica (0.040–0.063 mm; 300 g). Elution is carried out with ethyl acetate under a pressure of 0.5 bar (51 kPa), 75 cc fractions being collected. The first 7 fractions are discarded; the following 6 fractions are combined and concentrated to dryness under reduced pressure (20 mm Hg; 2.7 kPa) at 40° C. This yields a product (8 g) which is dissolved in a boiling mixture of ethyl acetate and hexane (40/60 by volume; 30 cc) to which decolorising charcoal (0.5 g) has been added. After hot filtration, the filtrate is cooled at 4° C. for 4 hours; the resulting crystals are filtered off, washed with an ethyl acetate/hexane mixture (40/60 by volume; 10 cc) and dried under reduced pressure (20 mm Hg; 2.7 kPa) at a temperature of about 20° C. in the presence of potassium hydroxide pellets. This yields 6-methyl-5-oxo-2,3,6,7-tetrahydro-5H-thiazolo[3,2-a]pyrimidine (3.9 g) in the form of white crystals melting at 76° C.

EXAMPLE 14

A solution of 3,3-dimethylacryloyl chloride (48.5 g) in chloroform (300 cc) is added dropwise, in the course of 15 minutes, to a solution of 2-amino-2-thiazoline (46.6 g) and triethylamine (54.5 cc) in chloroform (300 cc). The reaction mixture, the temperature of which is then 51° C., is subsequently heated under reflux for 17 hours. After cooling to about 20° C., the resulting crystals are filtered off and discarded. The organic filtrate is concentrated to dryness under reduced pressure (20 mm Hg; 2.7 kPa) at 40° C. and the residue is taken up in ethyl acetate (250 cc). The resulting crystals are once again filtered off, washed twice with ethyl acetate (100 cc in total) and discarded. The organic filtrates are combined and concentrated to dryness under reduced pressure (20 mm Hg; 2.7 kPa) and the residue is chromatographed on a column of diameter 7.5 cm containing silica (0.063–0.2 mm; 1.25 kg), elution being carried out with ethyl acetate and 500 cc fractions being collected. The first 9 fractions are discarded; the following 8 fractions are combined and concentrated to dryness under reduced pressure (20 mm Hg; 2.7 kPa) at 40° C. This yields a product (37 g) in the form of a light-chestnut coloured solid, which is dissolved in boiling ethyl acetate (190 cc) to which decolorising charcoal (0.3 g) has been added. After hot filtration, the filtrate is cooled at 4° C. for 2 hours. The resulting crystals are filtered off, washed twice with ethyl acetate cooled to about 5° C. (20 cc in tota) and discarded. The organic filtrates are combined and concentrated to dryness under reduced pressure (20 mm Hg; 2.7 kPa) and the residue is then dissolved in boiling diisopropyl ether (140 cc) to which decolorising charcoal (1 g) has been added. After hot filtration, the filtrate is cooled at 4° C. for 2 hours; the resulting crystals are filtered off, washed twice with diisopropyl ether cooled to about 5° C. (20 cc in total) and dried under reduced pressure (20 mm Hg; 2.7 kPa) at a temperature of about 20° C. in the presence of potassium hydroxide pellets. This yields a crude product (13.8 g) melting at 92° C. After dissolution in water (150 cc) and removal of the residual insoluble material by filtration, the filtrate is lyophilised. This yields a product (12.2 g) which is dissolved in boiling diisopropyl ether (110 cc). After cooling at 4° C. for 90 minutes, the resulting crystals are filtered off, washed twice with diisopropyl ether cooled to about 5° C. (20 cc in total) and dried under reduced pressure (20 mm Hg; 2.7 kPa) at a temperature of about 20° C. in the presence of potassium hydroxide pellets. This yields 7,7-dimethyl-5-oxo-2,3,6,7-tetrahydro-5H-thiazolo[3,2-a]pyrimidine (11.1 g) in the form of cream-coloured crystals melting at 90° C.

EXAMPLE 15

A solution of crotonoyl chloride (23.6 g) in chloroform (100 cc) is added dropwise, in the course of 20 minutes, to a solution of 2-amino-4-methyl-2-thiazoline (27.1 g) and triethylamine (31.8 cc) in chloroform (300 cc). The reaction mixture, the temperature of which is then 38° C., is subsequently heated under reflux for 3 hours. After cooling to about 40° C., the reaction mixture is concentrated to dryness under reduced pressure (20 mm Hg; 2.7 kPa) at 40° C. and the residue is then taken up in acetone (200 cc). The resulting crystals are filtered off, washed twice with acetone (20 cc in total) and discarded. The organic filtrates are combined and concentrated to dryness under reduced pressure (20 mm Hg; 2.7 kPa) at 40° C. and the residue is chromatographed on a column of diameter 4.2 cm containing silica (0.063–0.2 mm; 320 g). Elution is carried out with ethyl acetate, 250 cc fractions being collected. The first 6 fractions are discarded; the following 4 fractions are combined and concentrated to dryness under reduced pressure (20 mm Hg; 2.7 kPa). This yields a crude product (11.1 g) in the form of an oil, which is added to a product (4 g) prepared in the same manner in another operation, and the combined product is then divided into 3 equal batches to be chromatographed separately, in each case on a column of diameter 4 cm containing silica (0.040–0.063 mm; 150 g). Elution is carried out with a mixture of ethyl acetate and cyclohexane (90/10 by volume) under a pressure of 0.5 bar (51 kPa), 50 cc fractions being collected. The first 9 fractions are discarded; the following 9 fractions are combined and concentrated to dryness under reduced pressure (20 mm Hg; 2.7 kPa) at 40° C. This yields a product (8 g) which is dissolved in boiling diisopropyl ether (40 cc). After cooling at 4° C. for 1 hour, the resulting crystals are filtered off, washed with diisopropyl ether cooled to about 5° C. (10 cc) and dried under reduced pressure (20 mm Hg; 2.7 kPa) at a temperature of about 20° C. in the presence of potassium hydroxide pellets. This yields 3,7-dimethyl-5-oxo-2,3,6,7-tetrahydro-5H-thiazolo[3,2-a]pyrimidine (6.2 g) in the form of white crystals melting at 76° C.

EXAMPLE 16

A solution of (1-chlorocyclohexane)acetyl chloride (89 g) in chloroform (350 cc) is added dropwise, in the course of 35 minutes, to a solution of 2-amino-2-thiazoline (52.7 g) and triethylamine (130 cc) in chloroform (350 cc). The reaction mixture, the temperature of which is then 42° C., is subsequently heated under reflux for 16 hours. After cooling to about 20° C., the resulting crystals are filtered off and discarded. The organic filtrate is concentrated to dryness under reduced pressure (20 mm Hg; 2.7 kPa) at 40° C. and the residue is then taken up in acetone (400 cc). The resulting crystals are once again filtered off, washed twice with acetone (50 cc in total) and discarded. The organic filtrates are combined and concentrated to dryness under reduced pressure (20 mm Hg; 2.7 kPa) at 40° C. and the residue is chromatographed on a column of diameter 5 cm containing neutral alumina (0.12–0.15 mm; 880 g), elution being carried out with a mixture of ethyl acetate and cyclohexane (50/50 by volume) and 250 cc fractions being collected. The first 2 fractions are discarded; the following 3 fractions are combined and concentrated to dryness under reduced pressure (20 mm Hg; 2.7 kPa) at 40° C. This yields a crude product (35.6 g). This product is chromatographed a second time on a column of diameter 3.7 cm containing neutral alumina (0.12–0.15 mm; 360 g), elution being carried out with cyclohexane and 100 cc fractions being collected. After discarding the first 6 fractions and concentrating the following 9 fractions under reduced pressure (20 mm Hg; 2.7 kPa), a product (15 g) is obtained. Chromatography is carried out a third time on a column of diameter 6 cm containing silica (0.040–0.063 mm; 500 g), elution being carried out with a mixture of cyclohexane and ethyl acetate (45/55 by volume) under a pressure of 0.5 bar (51 kPa) and 100 cc fractions being collected. After discarding the first 12 fractions and concentrating the following 10 fractions under reduced pressure (20 mm Hg; 2.7 kPa), a yellow solid (5.4 g) is isolated, which is then dissolved in a boiling mixture of diisopropyl ether (60 cc) and acetonitrile (2 cc), to which decolorising charcoal (0.05 g) has been added. After hot filtration, the filtrate is cooled at 4° C. for 16 hours and the resulting crystals are filtered off, washed twice with diisopropyl ether cooled to about 5° C. (20 cc in total) and dried under reduced pressure (20 mm Hg; 2.7 kPa) at a temperature of about 20° C. in the presence of potassium hydroxide pellets. This finally yields 5-oxo-2,3,6,7-tetrahydrospiro{5H-thiazolo[3,2-a]pyrimidine-7,1'-cyclohexane} (4.4 g) in the form of white crystals melting at 110° C.

(1-Chlorocyclohexane)acetyl chloride can be prepared in the following manner:

Thionyl chloride (14.5 cc) is added dropwise, in the course of 15 minutes, to a solution of cyclohexan-1-ol-acetic acid (14 g) in chloroform (100 cc) and dimethylformamide (1 cc), and the mixture is then heated gradually to the reflux temperature until the evolution of gas ceases. The reaction mixture is then concentrated by distillation of the chloroform and the excess thionyl chloride under atmospheric pressure (about 760 mm Hg; 101 kPa). After the residue has been taken up with cyclohexane (50 cc) and the solution has been concentrated again under atmospheric pressure. (1-chlorocyclohexane)acetyl chloride (17.1 g) is obtained in the form of a chestnut-coloured oil.

EXAMPLE 17

A solution of 3-chloro-4,4,4-trifluorobutyryl chloride (48 g) in chloroform (150 cc) is added dropwise, in the course of 30 minutes, to a solution of 2-amino-2-thiazoline (27.8 g) and triethylamine (70 cc) in chloroform (400 cc). The reaction mixture, the temperature of which is then 60° C., is subsequently heated under reflux for 1 hour. After cooling to about 20° C., the resulting crystals are filtered off, washed twice with chloroform (40 cc in total) and discarded. The organic filtrates are combined and taken up in acetone (400 cc). The crystals which have appeared again are filtered off, washed twice with acetone (100 cc in total) and discarded. The organic filtrates are combined and concentrated to dryness under reduced pressure (20 mm Hg; 2.7 kPa) at 35° C. and the residue is chromatographed on a column of diameter 5 cm containing silica (0.063–0.2 mm; 700 g), elution being carried out with a mixture of ethyl acetate and cyclohexane (40/60 by volume) and 500 cc fractions being collected. The first fraction is discarded and the following 4 fractions are combined and concentrated to dryness under reduced pressure (20 mm Hg;

2.7 kPa) at 40° C. This yields a crude product (8 g) which is chromatographed on a column of diameter 4 cm containing silica (0.040-0.063 mm; 150 g). Elution is carried out with a mixture of ethyl acetate and cyclohexane (45/55 by volume) under a pressure of 0.5 bar (51 kPa), 10 cc fractions being collected. The first 16 fractions are discarded and the following 8 fractions are combined and concentrated to dryness under reduced pressure (20 mm Hg; 2.7 kPa) at 40° C. This yields a product (2 g). After the addition of a product (0.6 g) prepared in the same manner in another operation, dissolution in boiling diisopropyl ether (30 cc) to which decolorising charcoal (0.05 g) has been added, and hot filtration, the filtrate is cooled at 5° C. for 16 hours. The resulting crystals are filtered off, washed twice with diisopropyl ether cooled to about 5° C. (10 cc in total) and dried under reduced pressure (20 mm Hg; 2.7 kPa) at a temperature of about 20° C. in the presence of potassium hydroxide pellets. This yields 5-oxo-7-trifluoromethyl-2,3,6,7-tetrahydro-5H-thiazolo[3,2-a]pyrimidine (1.7 g) in the form of white crystals melting at 120° C.

The present invention also includes within its scope pharmaceutical compositions which comprise, as active ingredient, at least one compound of general formula (I) in association with any other pharmaceutically compatible product, which can be an inert carrier or diluent or physiologically active. The compositions according to the invention can be administered orally, parenterally or rectally.

Tablet, pills, powders (especially in gelatin capsules or in cachets) or granules can be used as solid compositions for oral administration. In these compositions, the active compound according to the invention is mixed with one or more inert diluents such as starch, cellulose, sucrose, lactose or silica. These compositions can also comprise substances other than diluents, e.g. one or more lubricants such as magnesium stearate or talc, a dyestuff, a coating (coated tablets) or a varnish.

Pharmaceutically acceptable solutions, suspensions, emulsions, syrups and elixirs containing inert diluents, such as water, ethanol, glycerol, vegetable oils or paraffin oil, can be used as liquid compositions for oral administration. These compositions can also comprise substances other than diluents, e.g. wetting, sweetening, thickening, flavouring or stabilising agents.

Sterile compositions for parenteral administration are preferably suspensions, emulsions or aqueous or non-aqueous solutions. Water, propylene glycol, a polyethylene glycol, vegetable oils, in particular olive oil, injectable organic esters, e.g. ethyl oleate, or other suitable organic solvents can be employed as the solvent or vehicle. These liquid compositions can also contain adjuvants, in particular wetting agents, agents for creating isotonicity, emulsifiers, dispersing agents and stabilisers. Sterilisation can be carried out in several ways, e.g. by aseptic filtration, by incorporating sterilising agents into the composition, by irradiation or by heating. The compositions can also be prepared in the form of sterile solid compositions which can be dissolved in an injectable sterile medium at the time of use.

Compositions for rectal administration are suppositories or rectal capsules which contain, in addition to the active ingredient, excipients such as cacoa butter, semi-synthetic glycerides or polyethylene glycols.

In human therapy, the compounds of general formula (I) are particularly useful in the basic treatment of rheumatic disease and allergic states, and as analgesics. The doses depend on the desired effect and the duration of the treatment; adult doses are generally between 50 and 1000 mg per day, administered orally in one or more portions.

In general, the physician will decide the posology considered most appropriate taking into account the age, the weight and all the other factors intrinsic to the patient being treated.

The following Examples illustrate pharmaceutical compositions according to the invention.

EXAMPLE 18

Tablets containing 50 mg doses of active ingredient and having the following composition are prepared in accordance with the usual technique:

| | |
|---|---|
| 5-oxo-2,3,6,7-tetrahydro-spiro{5H—thiazolo-[3,2-a]pyrimidine-7,1'-cyclohexane} | 50 mg |
| starch | 60 mg |
| lactose | 50 mg |
| magnesium stearate | 2 mg |

EXAMPLE 19

Tablets containing 50 mg doses of active ingredient and having the following composition are prepared in accordance with the usual technique:

| | |
|---|---|
| 7-methyl-5-oxo-2,3,6,7-tetrahydro-5H—thiazolo[3,2-a]pyrimidine | 50 mg |
| starch | 15 mg |
| colloidal silica | 9.5 mg |
| magnesium stearate | 0.5 mg |

We claim:

1. A 2,3,6,7-tetrahydrothiazolo[3,2-a]-pyrimidine compound of the formula:

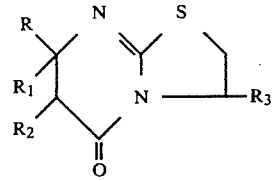

wherein R represents phenyl, alkyl of 1 through 4 carbon atoms, alkenyl of 2 through 4 carbon atoms or cycloalkyl of 3 through 6 carbon atoms and $R_1$ represents hydrogen, or R and $R_1$ each represent phenyl or unsubstituted alkyl of 1 through 4 carbon atoms, or R and $R_1$ together represent an alkylene radical of 4 or 5 carbon atoms, and $R_2$ and $R_3$ each represent hydrogen or an unsubstituted alkyl radical of 1 through 4 carbon atoms, or R and $R_1$ each represent hydrogen and one of $R_2$ and $R_3$ represents hydrogen and the other represents unsubstituted alkyl of 1 through 4 carbon atoms, or $R_2$ and $R_3$ both represent unsubstituted alkyl of 1 through 4 carbon atoms.

2. A compound according to claim 1 wherein R represents unsubstituted alkyl of 1 through 4 carbon atoms, phenyl, or cycloalkyl of 3 through 6 carbon atoms and $R_1$ represents hydrogen, or alternatively R and $R_1$ together form an alkylene radical of 4 or 5 carbon atoms, and $R_2$ and $R_3$ each represent hydrogen or methyl.

3. A compound according to claim 1 wherein R represents methyl, ethyl, phenyl or cyclohexyl, and $R_1$ represents hydrogen, or alternatively R and $R_1$ together represent the pentamethylene radical, $R_2$ represents hydrogen and $R_3$ represents hydrogen or methyl.

4. A compound according to claim 1 wherein R represents phenyl or unsubstituted alkyl of 1 through 4 carbon atoms, and $R_1$, $R_2$ and $R_3$ represent hydrogen.

5. A compound according to claim 1 which is 7-methyl-5-oxo-2,3,6,7-tetrahydro-5H-thiazolo[3,2-a]pyrimidine.

6. A compound according to claim 1 which is 7-ethyl-5-oxo-2,3,6,7-tetrahydro-5H-thiazolo[3,2-a]-pyrimidine.

7. A compound according to claim 1 which is 7-cyclohexyl-5-oxo-2,3,6,7-tetrahydro-5H-thiazolo-[3,2-a]pyrimidine.

8. A compound according to claim 1 which is 5-oxo-2,3,6,7-tetrahydro-spiro{5H-thiazolo[3,2-a]-pyrimidine-7,1'-cyclohexane}.

9. A compound according to claim 1 which is 3,7-dimethyl-5-oxo-2,3,6,7-tetrahydro-5H-thiazolo-[3,2-a]pyrimidine.

10. A compound according to claim 1 which is 5-oxo-7-phenyl-2,3,6,7-tetrahydro-5H-thiazolo[3,2-a]-pyrimidine.

11. A pharmaceutical composition useful in the treatment of rheumatic disease which comprises an effective amount of a thiazolo[3,2-a]pyrimidine compound of the general formula depicted in claim 1, wherein R, $R_1$, $R_2$ and $R_3$ are as defined in claim 1, in association with a pharmaceutically acceptable carrier or diluent.

* * * * *